(12) United States Patent
Matheny

(10) Patent No.: US 11,969,339 B2
(45) Date of Patent: Apr. 30, 2024

(54) PROSTHETIC TISSUE VALVES

(71) Applicant: CorMatrix Cardiovascular, Inc., Roswell, GA (US)

(72) Inventor: Robert G Matheny, Norcross, GA (US)

(73) Assignee: CorMatrix Cardiovascular, Inc., Roswell, GA (US)

( * ) Notice: Subject to any disclaimer, the term of this patent is extended or adjusted under 35 U.S.C. 154(b) by 703 days.

(21) Appl. No.: 17/177,001

(22) Filed: Feb. 16, 2021

(65) Prior Publication Data

US 2021/0161656 A1 Jun. 3, 2021

Related U.S. Application Data

(63) Continuation of application No. 16/129,968, filed on Sep. 13, 2018, now Pat. No. 10,952,843, and a continuation-in-part of application No. 15/206,833, filed on Jul. 11, 2016, now Pat. No. 10,188,510, and a continuation-in-part of application No. 14/960,354, filed on Dec. 5, 2015, now Pat. No. 9,907,649, and a continuation-in-part of application No. 14/229,854, filed on Mar. 29, 2014, now Pat. No. 9,308,084.

(51) Int. Cl.
*A61F 2/24* (2006.01)
*A61L 27/36* (2006.01)
*A61L 27/38* (2006.01)
*A61L 27/50* (2006.01)

(52) U.S. Cl.
CPC ........ *A61F 2/2412* (2013.01); *A61L 27/3604* (2013.01); *A61L 27/3629* (2013.01); *A61L 27/3633* (2013.01); *A61L 27/3826* (2013.01); *A61L 27/3834* (2013.01); *A61L 27/50* (2013.01); *A61F 2/2409* (2013.01); *A61F 2/2457* (2013.01); *A61F 2/246* (2013.01); *A61F 2210/0014* (2013.01); *A61F 2220/0075* (2013.01); *A61F 2230/0067* (2013.01); *A61L 27/367* (2013.01); *A61L 27/3873* (2013.01); *A61L 2300/104* (2013.01); *A61L 2300/404* (2013.01); *A61L 2300/406* (2013.01); *A61L 2300/41* (2013.01); *A61L 2300/414* (2013.01); *A61L 2300/416* (2013.01); *A61L 2300/42* (2013.01); *A61L 2300/606* (2013.01); *A61L 2430/20* (2013.01)

(58) Field of Classification Search
CPC .. A61F 2/2412; A61F 2/2457; A61L 27/3629; A61L 27/3633; A61L 27/3873
See application file for complete search history.

(56) References Cited

U.S. PATENT DOCUMENTS

2014/0330369 A1* 11/2014 Matheny ............... A61F 2/2412
623/2.14

* cited by examiner

*Primary Examiner* — Suba Ganesan
(74) *Attorney, Agent, or Firm* — Thomas | Horstemeyer, LLP

(57) ABSTRACT

A prosthetic valve comprising a tubular shaped sheet member comprising an extracellular matrix (ECM) composition, the sheet member having a plurality of ribbons having proximal and distal ends, the distal ends of the ribbons projecting from the sheet member proximal end.

9 Claims, 13 Drawing Sheets

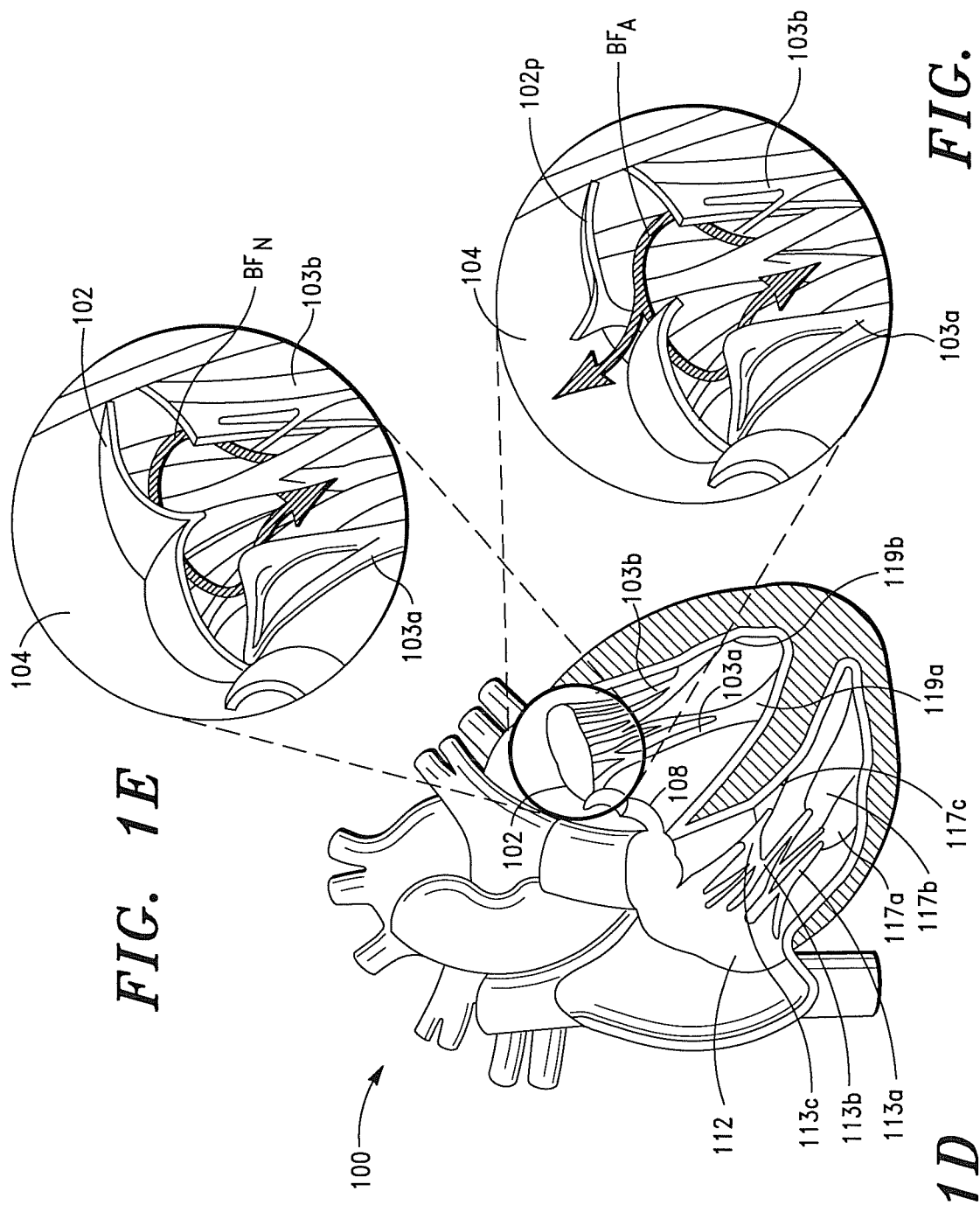

A-A

PROSTHETIC TISSUE VALVES

CROSS-REFERENCE TO RELATED APPLICATIONS

This application is a continuation of U.S. application Ser. No. 16/129,968, filed on Sep. 13, 2018, which is a continuation-in-part of U.S. application Ser. No. 15/206,833, filed on Jul. 11, 2016, now U.S. Pat. No. 10,188,510, which is a continuation-in-part application of U.S. application Ser. No. 14/960,354, filed on Dec. 5, 2015, now U.S. Pat. No. 9,907,649, which is a continuation-in-part application of U.S. application Ser. No. 14/229,854, filed on Mar. 29, 2014, now U.S. Pat. No. 9,308,084, which claims priority to U.S. Provisional Application No. 61/819,232, filed on May 3, 2013.

FIELD OF THE INVENTION

The present invention generally relates to prosthetic valves for replacing defective cardiovascular valves. More particularly, the present invention relates to prosthetic atrioventricular valves and methods for anchoring same to cardiovascular structures and/or tissue.

BACKGROUND OF THE INVENTION

As is well known in the art, the human heart has four valves that control blood flow circulating through the human body. Referring to FIGS. 1A and 1B, on the left side of the heart 100 is the mitral valve 102, located between the left atrium 104 and the left ventricle 106, and the aortic valve 108, located between the left ventricle 106 and the aorta 110. Both of these valves direct oxygenated blood from the lungs into the aorta 110 for distribution through the body.

The tricuspid valve 112, located between the right atrium 114 and the right ventricle 116, and the pulmonary valve 118, located between the right ventricle 116 and the pulmonary artery 120, however, are situated on the right side of the heart 100 and direct deoxygenated blood from the body to the lungs.

Referring now to FIGS. 1C and 1D, there are also generally five papillary muscles in the heart 100; three in the right ventricle 116 and two in the left ventricle 106. The anterior, posterior and septal papillary muscles 117a, 117b, 117c of the right ventricle 116 each attach via chordae tendineae 113a, 113b, 113c to the tricuspid valve 112. The anterior and posterior papillary muscles 119a, 119b of the left ventricle 106 attach via chordae tendineae 103a, 103b to the mitral valve 102 (see also FIG. 1E).

Since heart valves are passive structures that simply open and close in response to differential pressures, the issues that can develop with valves are typically classified into two categories: (i) stenosis, in which a valve does not open properly, and (ii) insufficiency (also called regurgitation), in which a valve does not close properly.

Stenosis and insufficiency can occur as a result of several abnormalities, including damage or severance of one or more chordae or several disease states. Stenosis and insufficiency can also occur concomitantly in the same valve or in different valves.

Both of the noted valve abnormalities can adversely affect organ function and result in heart failure. By way of example, referring first to FIG. 1E, there is shown normal blood flow (denoted "BFN") proximate the mitral valve 102 during closure. Referring now to FIG. 1F, there is shown abnormal blood flow (denoted "$BF_A$") or regurgitation caused by a prolapsed mitral valve 102p. As illustrated in FIG. 1F, the regurgitated blood "$BF_A$" flows back into the left atrium, which can, if severe, result in heart failure.

In addition to stenosis and insufficiency of a heart valve, surgical intervention may also be required for certain types of bacterial or fungal infections, wherein the valve may continue to function normally, but nevertheless harbors an overgrowth of bacteria (i.e. "vegetation") on the valve leaflets. The vegetation can, and in many instances will, flake off (i.e., "embolize") and lodge downstream in a vital artery.

If such vegetation is present on the valves of the left side (i.e., the systemic circulation side) of the heart, embolization can, and often will, result in sudden loss of the blood supply to the affected body organ and immediate malfunction of that organ. The organ most commonly affected by such embolization is the brain, in which case the patient can, and in many instances will, suffer a stroke.

Likewise, bacterial or fungal vegetation on the tricuspid valve can embolize to the lungs. The noted embolization can, and in many instances will, result in lung dysfunction.

Treatment of the noted heart valve dysfunctions typically comprises reparation of the diseased heart valve with preservation of the patient's own valve or replacement of the valve with a mechanical or bioprosthetic valve, i.e., a prosthetic valve.

Various prosthetic valves; particularly, prosthetic heart valves have thus been developed for replacement of native diseased or defective heart valves. The selection of a particular type of replacement valve depends on many factors, such as the location of the diseased or defective native valve, the age and other specifics of the recipient of the replacement heart valve, and the surgeon's experiences and preferences.

Commonly used replacement heart valves are typically classified in the following three groups: (i) mechanical valves, (ii) allograft tissue valves, and (iii) xenograft tissue valves. Each of the noted valves and disadvantages associated with same are discussed in detail below.

Mechanical Heart Valves

As is well known in the art, mechanical heart valves, such as caged-ball valves, bi-leaflet valves, and tilting disk valves, typically comprise various metal and polymeric components, which can, and in most instances will, induce an adverse inflammatory response when implanted in a patient or subject.

A further disadvantage associated with mechanical heart valves is that such valves also have a propensity to cause the formation of blood clots after implantation in a patient. If such blood clots form on the mechanical valve, they can preclude the valve from opening or closing correctly or, more importantly, can disengage from the valve and embolize to the brain, causing an embolic stroke. Thus, recipients of a mechanical heart valve are typically required to take systemic anticoagulant drugs for the rest of their lives. In addition to being expensive, these anticoagulant drugs can themselves be dangerous in that they can cause abnormal bleeding in the recipient or patient that can lead to a hemorrhagic stroke.

Allograft Tissue Valves

As is also well known in the art, allograft tissue valves are harvested from human sources, such as human cadavers. Unlike mechanical heart valves, allograft tissue valves typically do not promote blood clot formation and, therefore, avoid the need for prescribing an anticoagulant medication for the recipient or patient. However, there are still several drawbacks and disadvantages associated with allograft tissue valves.

A major drawback of allograft tissue valves is that such valves are not available in sufficient numbers to satisfy the needs of all patients who need new heart valves.

A further major drawback of allograft tissue valves is that recipients of allograft tissue valves, i.e., patients, are typically required to take systemic antirejection and/or immunosuppressive drugs for a predetermined period of time and, in some instances, for a lifetime. Although antirejection and/or immunosuppressive drugs increase the possibility that a patient will accept an allograft without complications, the drugs will often leave the recipient vulnerable to a plurality of other infectious diseases, including bacterial infections, fungal infections, viral infections and the like.

Xenograft Tissue Valves

As is additionally well known in the art, xenograft tissue valves are formed from non-human tissue sources, such as cows or pigs. Xenograft tissue valves are similarly less likely to cause blood clot formation than comparable mechanical valves. However, there are also several drawbacks and disadvantages associated with most conventional allograft tissue valves.

A major drawbacks of conventional xenograft tissue valves is that such valves often comprise glutaraldehyde processed tissue and, hence, are prone to calcification and lack the long-term durability of mechanical valves.

More recently, remodelable xenograft tissue valves comprising decellularized extracellular matrix (ECM) have been developed and employed to replace various heart valves. Such valves are not prone to calcification and, as set forth in Applicant's U.S. Pat. Nos. 9,308,084, 9,011,526, 8,709,076 and Co-pending U.S. application Ser. No. 16/129,968, which are expressly incorporated by reference herein in their entirety, have the capacity to remodel, i.e., form valve structures similar to native valve structures when implanted in a patient, and induce remodeling of native cardiovascular tissue and regeneration of new cardiovascular tissue when implanted in a patient.

Although most remodelable xenograft ECM tissue valves substantially reduce and, in most instances, eliminate the major disadvantages and drawbacks associated with mechanical valves, allograft tissue valves, and conventional xenograft tissue valves, a drawback associated with some remodelable xenograft tissue valves is that, by virtue of their shape and required attachment to a valve annulus region; particularly, a mitral valve annulus region, and a cardiovascular structure, such as the papillary muscles, is disruption of blood flow into and, hence, through the other valves, e.g., aortic valve.

A further disadvantage is that a higher valvular pressure gradient can, and often will be generated across the valve annulus region.

There thus remains a need for improved prosthetic xenograft tissue valves with minimal in vivo calcification and cytotoxicity, and optimum blood flow modulation and characteristics.

It is therefore an object of the present invention to provide improved prosthetic xenograft tissue valves with minimal in vivo calcification and cytotoxicity.

It is another object of the present invention to provide prosthetic xenograft tissue valves with improved blood flow modulation and characteristics.

It is another object of the present invention to provide improved prosthetic xenograft tissue valves that induce host tissue proliferation, bioremodeling and regeneration of new tissue and tissue structures with site-specific structural and functional properties.

It is another object of the present invention to provide improved prosthetic xenograft tissue valves that induce adaptive regeneration.

It is another object of the present invention to provide improved prosthetic xenograft tissue valves that are capable of administering a pharmacological agent to host tissue and, thereby produce a desired biological and/or therapeutic effect.

It is yet another object of the present invention to provide methods for replacing diseased or defective native heart valves with improved prosthetic tissue valves.

SUMMARY OF THE INVENTION

The present invention is directed to prosthetic tissue valves that can be readily employed to selectively replace diseased or defective heart valves, and methods for attaching (or anchoring) same to cardiovascular structures and/or tissue.

In a preferred embodiment of the invention, the prosthetic tissue valves comprise continuous tubular structures.

In some embodiments of the invention, the proximal end of the prosthetic tissue valves comprise an annular ring that is designed and configured to securely engage the prosthetic tissue valves to a valve annulus and, hence, cardiovascular tissue associated therewith.

According to the invention, the prosthetic tissue valves can comprise various biocompatible materials.

In some embodiments of the invention, the prosthetic tissue valves comprise an ECM composition comprising acellular ECM derived from a mammalian tissue source.

In a preferred embodiment of the invention, the mammalian tissue source is selected from the group comprising small intestine submucosa (SIS), urinary bladder submucosa (UBS), stomach submucosa (SS), urinary basement membrane (UBM), liver basement membrane (LBM), mesothelial tissue, placental tissue and cardiac tissue.

In some embodiments of the invention, the ECM composition (and, hence, prosthetic tissue valves formed therefrom) further comprises at least one additional biologically active agent or composition, i.e., an agent that induces or modulates a physiological or biological process, or cellular activity, e.g., induces proliferation, and/or growth and/or regeneration of tissue.

In some embodiments of the invention, the biologically active agent comprises a growth factor, including, without limitation, transforming growth factor alpha (TGF-α), transforming growth factor beta (TGF-β), fibroblast growth factor-2 (FGF-2), and vascular endothelial growth factor (VEGF).

In some embodiments of the invention, the biologically active agent comprises a cell, including, without limitation, a human embryonic stem cell and mesenchymal stem cell.

In some embodiments of the invention, the ECM composition (and, hence, tubular members formed therefrom) further comprises a statin, i.e., a HMG-CoA reductase inhibitor.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIGS. 1A-1D are schematic illustrations of a human heart;

FIG. 1E is an illustration of a normal mitral valve;

FIG. 1F is an illustration of a prolapsed mitral valve;

DETAILED DESCRIPTION OF THE PREFERRED EMBODIMENT

Figure 1A:
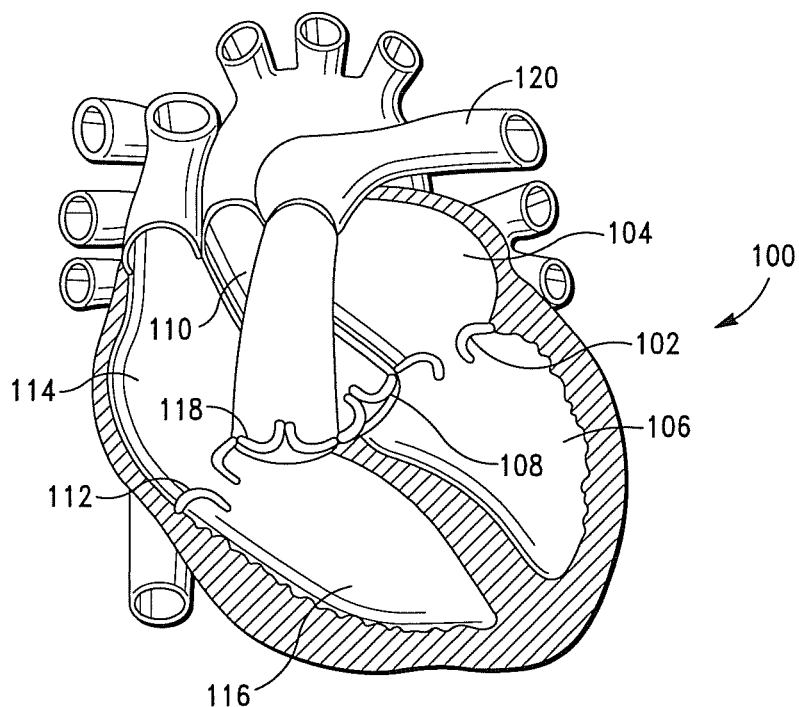
Figure 1B:
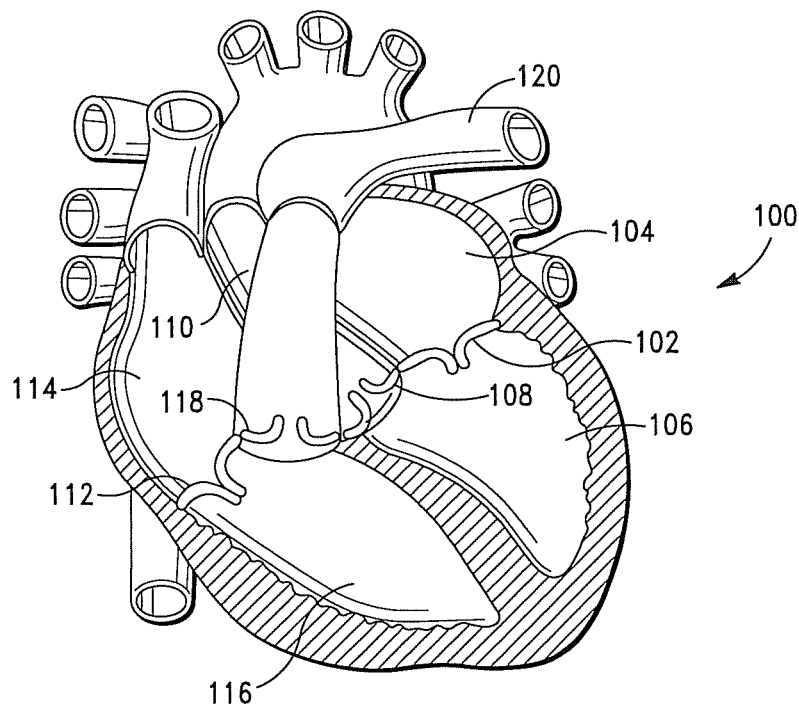
Figure 1C:
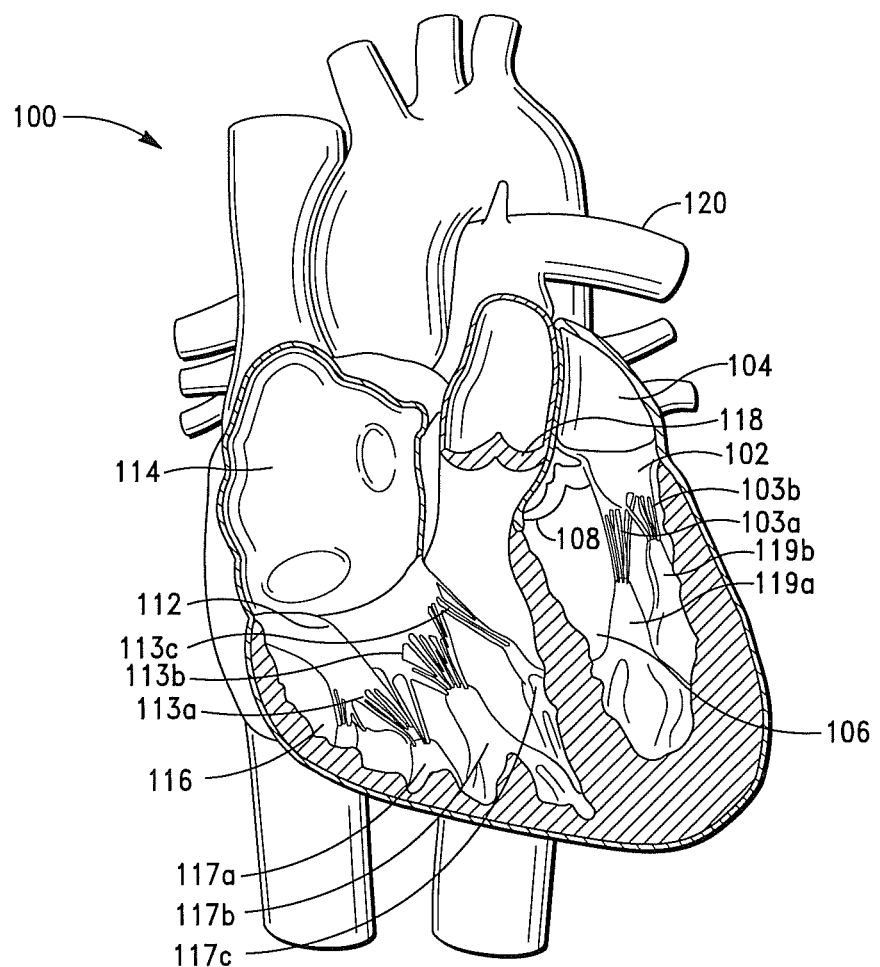

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "a pharmacological agent" includes two or more such agents and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "extracellular matrix", "ECM", and "ECM material" are used interchangeably herein, and mean and include a collagen-rich substance that is found in between cells in mammalian tissue, and any material processed therefrom, e.g., decellularized ECM.

The term "acellular ECM", as used herein, means and includes ECM that has a reduced content of cells.

According to the invention, ECM can be derived from a variety of mammalian tissue sources, including, without limitation, small intestine submucosa (SIS), urinary bladder submucosa (UBS), stomach submucosa (SS), central nervous system tissue, epithelium of mesodermal origin, i.e. mesothelial tissue, dermal tissue, subcutaneous tissue, gastrointestinal tissue, i.e., large and small intestines, tissue surrounding growing bone, placental tissue, omentum tissue, cardiac tissue, e.g., pericardium and/or myocardium, kidney tissue, pancreas tissue, lung tissue and combinations thereof. The ECM material can also comprise collagen from mammalian sources.

The terms "urinary bladder submucosa (UBS)", "small intestine submucosa (SIS)" and "stomach submucosa (SS)" also mean and include any UBS and/or SIS and/or SS material that includes the tunica mucosa (which includes the transitional epithelial layer and the tunica propria), submucosal layer, one or more layers of muscularis, and adventitia (a loose connective tissue layer) associated therewith.

According to the invention, ECM can also be derived from basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

Additional sources of mammalian basement membrane include, without limitation, spleen, lymph nodes, salivary glands, prostate, pancreas and other secreting glands.

According to the invention, ECM can also be derived from other sources, including, without limitation, collagen from plant sources and synthesized extracellular matrices, i.e., cell cultures.

The term "angiogenesis", as used herein, means a physiologic process involving the growth of new blood vessels from pre-existing blood vessels.

The term "neovascularization", as used herein, means and includes the formation of functional vascular networks that can be perfused by blood or blood components. Neovascularization includes angiogenesis, budding angiogenesis, intussusceptive angiogenesis, sprouting angiogenesis, therapeutic angiogenesis and vasculogenesis.

The term "biologically active agent", as used herein, means and includes agent that induces or modulates a physiological or biological process, or cellular activity, e.g., induces proliferation, and/or growth and/or regeneration of tissue.

The term "biologically active agent" thus means and includes, without limitation, the following growth factors: epidermal growth factor (EGF), transforming growth factor alpha (TGF-α), transforming growth factor beta (TGF-β), fibroblast growth factor-2 (FGF-2), vascular endothelial growth factor (VEGF), hepatocyte growth factor (HGF), insulin-like growth factor (IGF), nerve growth factor (NGF), platelet derived growth factor (PDGF), tumor necrosis factor alpha (TNF-α) and placental growth factor (PLGF).

The term "biologically active agent" also means and includes, without limitation, human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogeneic cells, allogeneic cells and post-natal stem cells.

The term "biologically active agent" also means and includes, without limitation, the following biologically active agents (referred to interchangeably herein as a "protein", "peptide" and "polypeptide"): collagen (types I-V), proteoglycans, glycosaminoglycans (GAGs), glycoproteins, growth factors, cytokines, cell-surface associated proteins, cell adhesion molecules (CAM), angiogenic growth factors, endothelial ligands, matrikines, cadherins, immuoglobins, fibril collagens, non-fibrillar collagens, basement membrane collagens, multiplexins, small-leucine rich proteoglycans, decorins, biglycans, fibromodulins, keratocans, lumicans, epiphycans, heparin sulfate proteoglycans, perlecans, agrins, testicans, syndecans, glypicans, serglycins, selectins, lecticans, aggrecans, versicans, neurocans, brevicans, cytoplasmic domain-44 (CD-44), macrophage stimulating factors, amyloid precursor proteins, heparins, chondroitin sulfate B (dermatan sulfate), chondroitin sulfate A, heparin sulfates, hyaluronic acids, fibronectins, tenascins, elastins, fibrillins, laminins, nidogen/enactins, fibulin I, fibulin II, integrins, transmembrane molecules, thrombospondins, osteopontins and angiotensin converting enzymes (ACE).

The term "biologically active composition", as used herein, means and includes a composition comprising a "biologically active agent".

The terms "pharmacological agent", "active agent" and "drug" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent" and "drug" thus mean and include, without limitation, antibiotics, anti-arrhythmic agents, anti-viral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPs), enzymes and enzyme inhibitors, anticoagulants and/or anti-thrombotic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The teams "pharmacological agent", "active agent" and "drug" also mean and include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, anti-VEGFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), NT-3, NT-4, NGF and IGF-2.

The terms "pharmacological agent", "active agent" and "drug" also mean and include the following Class I-Class V antiarrhythmic agents: (Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent", "active agent" and "drug" also mean and include, without limitation, the following antibiotics: aminoglycosides, cephalosporins, chloramphenicol, clindamycin, erythromycins, fluoroquinolones, macrolides, azolides, metronidazole, penicillins, tetracyclines, trimethoprim-sulfamethoxazole and vancomycin.

The terms "pharmacological agent", "active agent" and "drug" also mean and include, without limitation, the following steroids: andranes (e.g., testosterone), cholestanes, cholic acids, corticosteroids (e.g., dexamethasone), estraenes (e.g., estradiol) and pregnanes (e.g., progesterone).

The terms "pharmacological agent", "active agent" and "drug" also mean and include one or more classes of narcotic analgesics, including, without limitation, morphine, codeine, heroin, hydromorphone, levorphanol, meperidine, methadone, oxycodone, propoxyphene, fentanyl, methadone, naloxone, buprenorphine, butorphanol, nalbuphine and pentazocine.

The terms "pharmacological agent", "active agent" and "drug" also mean and include one or more classes of topical or local anesthetics, including, without limitation, esters, such as benzocaine, chloroprocaine, cocaine, cyclomethycaine, dimethocaine/larocaine, piperocaine, propoxycaine, procaine/novacaine, proparacaine, and tetracaine/amethocaine. Local anesthetics can also include, without limitation, amides, such as articaine, bupivacaine, cinchocaine/dibucaine, etidocaine, levobupivacaine, lidocaine/lignocaine, mepivacaine, prilocaine, ropivacaine, and trimecaine. Local anesthetics can further include combinations of the above from either amides or esters.

As indicated above, the terms "pharmacological agent", "active agent" and "drug" also mean and include an anti-inflammatory.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e., the protective tissue response to injury or destruction of tissues, which serves to destroy, dilute, or wall off both the injurious agent and the injured tissues.

Anti-inflammatory agents thus include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin and zomepirac sodium.

The terms "pharmacological agent", "active agent" and "drug" also mean and include a statin, i.e. a HMG-CoA reductase inhibitor, including, without limitation, atorvastatin (Lipitor®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Crestor®) and simvastatin (Zocor®, Lipex®).

The term "pharmacological composition", as used herein, means and includes a composition comprising a "pharmacological agent" and/or any additional agent or component identified herein.

The term "therapeutically effective", as used herein, means that the amount of the "pharmacological agent" and/or "biologically active agent" and/or "pharmacological composition" and/or "biologically active composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As stated above, the present invention is directed to prosthetic tissue valves that can be readily employed to selectively replace diseased or defective native heart valves, and methods for attaching (or anchoring) same to cardiovascular structures and/or tissue.

As discussed in detail below, in a preferred embodiment of the invention, the prosthetic tissue valves comprise continuous tubular structures or members.

As indicated above, in some embodiments of the invention, the proximal ends of the prosthetic tissue valves of the invention comprise an annular ring that is designed and configured to securely engage the prosthetic tissue valves to a valve annulus (and, hence, cardiovascular tissue associated therewith).

In some embodiments of the invention, the annular ring comprises at least one anchoring mechanism that is configured to position the prosthetic tissue valves proximate a valve annulus, and maintain contact therewith for a predetermined anchor support time period.

According to the invention, the anchoring mechanisms can comprise various forms and materials, such as the anchoring mechanisms disclosed in U.S. Pat. No. 9,044,319, which is incorporated by reference herein in its entirety.

In some embodiments of the invention, the anchoring mechanisms are configured to position ECM prosthetic tissue valves of the invention proximate a valve annulus, and maintain contact therewith for a predetermined temporary anchor support period of time within the process of tissue regeneration.

In some embodiments of the invention, the prosthetic tissue valves comprise continuous conical shaped structural members.

According to the invention, the prosthetic tissue valves can comprise various biocompatible materials and compositions formed therefrom.

In a preferred embodiment of the invention, the prosthetic tissue valves comprise sheet members.

According to the invention, the prosthetic tissue valves can comprise single or multi-sheet members.

According to the invention, the sheet(s) can be formed into the tubular and conical shaped members of the invention and secured about the mating edges by various conventional means, e.g., suturing the mating edges together.

In some embodiments of the invention, the prosthetic tissue valves comprise an ECM composition comprising ECM derived from a mammalian tissue source.

According to the invention, the ECM can be derived from various mammalian tissue sources and methods for preparing same, such as disclosed in U.S. Pat. Nos. 7,550,004, 7,244,444, 6,379,710, 6,358,284, 6,206,931, 5,733,337 and 4,902,508 and U.S. application Ser. No. 12/707,427, now U.S. Pat. No. 8,980,296; which are incorporated by reference herein in their entirety.

According to the invention, the mammalian tissue sources include, without limitation, the small intestine, large intestine, stomach, lung, liver, kidney, pancreas, peritoneum, placenta, heart, bladder, prostate, tissue surrounding growing enamel, tissue surrounding growing bone, and any fetal tissue from any mammalian organ.

The mammalian tissue can thus comprise, without limitation, small intestine submucosa (SIS), urinary bladder submucosa (UBS), stomach submucosa (SS), central nervous system tissue, epithelium of mesodermal origin, i.e. mesothelial tissue, dermal tissue, subcutaneous tissue, gastrointestinal tissue, i.e., large and small intestines, tissue surrounding growing bone, placental tissue, omentum tissue, cardiac tissue, e.g., pericardium and/or myocardium, kidney tissue, pancreas tissue, lung tissue, and combinations thereof. The ECM can also comprise collagen from mammalian sources.

In some embodiments, the mammalian tissue source comprises an adolescent mammalian tissue source, e.g., tissue derived from a porcine mammal less than 3 years of age.

According to the invention, the ECM can also be derived from the same or different mammalian tissue sources, as disclosed in Co-Pending application Ser. Nos. 13/033,053 and 13/033,102; which are incorporated by reference herein.

In a preferred embodiment of the invention, the ECM comprises sterilized and decellularized (or acellular) ECM.

According to the invention, the ECM can be sterilized and decellularized by various conventional means.

In some embodiments of the invention, the ECM is sterilized and decellularized via applicant's proprietary process disclosed in Co-Pending U.S. application Ser. No. 13/480,205; which is expressly incorporated by reference herein in its entirety.

In some embodiments of the invention, the ECM comprises crosslinked ECM. According to the invention, the ECM can be crosslinked by various conventional materials and methods.

It is contemplated that, following placement of a prosthetic tissue valve comprising an ECM composition (hereinafter "an ECM prosthetic tissue valve") on a cardiovascular structure (or structures) in a subject, e.g., valve annulus, and, hence, cardiovascular tissue associated therewith, the ECM prosthetic tissue valve will induce "modulated healing" of the cardiovascular structure(s) and tissue associated therewith.

It is also contemplated that, following placement of an ECM prosthetic tissue valve on a cardiovascular structure (or structures) in a subject, the ECM prosthetic tissue valve will become populated with cells from the subject that will gradually remodel the ECM into cardiovascular tissue and tissue (and, hence, valve) structures.

It is further contemplated that, following placement of an ECM prosthetic tissue valve on a cardiovascular structure (or structures) in a subject, stem cells will migrate to the ECM prosthetic tissue valve from the point(s) at which the valve is attached to the cardiovascular structure, e.g., valve annulus, or structures, e.g., valve annulus and heart wall.

It is still further contemplated that the points at which an ECM prosthetic tissue valve is attached to a cardiovascular structure (or structures) in a subject will serve as points of constraint that direct the remodeling of the ECM into cardiovascular tissue and valve structures that are identical or substantially identical to properly functioning native cardiovascular tissue and valve structures.

It is still further contemplated that, during circulation of epithelial and endothelial progenitor cells after placement of an ECM prosthetic tissue valve on a cardiovascular structure (or structures), the surfaces of an ECM prosthetic tissue valve will rapidly become lined or covered with epithelial and/or endothelial progenitor cells.

As indicated above, in some embodiments of the invention, the proximal ends of the prosthetic tissue valves of the invention comprise an annular ring that is designed and configured to securely engage the prosthetic tissue valves to a valve annulus (and, hence, cardiovascular tissue associated therewith).

As also indicated above, in some embodiments, the distal end of prosthetic tissue valves comprising a conical shaped structural member further comprise a structural ring.

According to the invention, the annular ring and structural ring can also comprise various biocompatible materials and compositions formed therefrom. Suitable biocompatible ring materials are disclosed in U.S. application Ser. No. 14/953,548, which is incorporated by reference herein.

In some embodiments of the invention, the annular ring and/or structural ring comprise a polymeric composition comprising a biodegradable polymeric material. According to the invention, suitable biodegradable polymeric materials comprise, without limitation, polycaprolactone (PCL), Artelon® (porous polyurethaneurea), polyglycolide (PGA), polylactide (PLA), poly(s-caprolactone) (PCL), polydioxanone (a polyether-ester), polylactide-co-glycolide, polyamide esters, polyalkalene esters, polyvinyl esters, polyvinyl alcohol and polyanhydrides.

According to the invention, the polymeric composition can further comprise a natural polymer, including, without limitation, polysaccharides (e.g., starch and cellulose), proteins (e.g., gelatin, casein, silk, wool, etc.), and polyesters (e.g., polyhydroxyalkanoates).

The polymeric composition can also comprise a hydrogel composition, including, without limitation, polyurethane, poly(ethylene glycol), poly(propylene glycol), poly(vinylpyrrolidone), xanthan, methyl cellulose, carboxymethyl cellulose, alginate, hyaluronan, poly(acrylic acid), polyvinyl alcohol, acrylic acid, hydroxypropyl methyl cellulose, methacrylic acid, αβ-glycerophosphate, κ-carrageenan, 2-acrylamido-2-methylpropanesulfonic acid and β-hairpin peptide.

According to the invention, the polymeric composition can further comprise a non-biodegradable polymer, including, without limitation, polytetrafluoroethylene (Teflon®) and polyethylene terephthalate (Dacron®).

In some embodiments of the invention, the polymeric composition comprises poly(urethane urea); preferably, Artelon® distributed by Artimplant AB in Goteborg, Sweden.

In some embodiments, the polymeric composition comprises poly(glycerol sebacate) (PGS).

In some embodiments of the invention, annular ring and/or structural ring comprise a biocompatible metal. According to the invention, suitable metals comprise, without limitation, Nitinol®, stainless steel and magnesium.

In some embodiments, the annular ring and/or structural ring also comprise an ECM composition comprising acellular ECM derived from a mammalian tissue source.

As stated above, in some embodiments of the invention, the ECM composition (and, hence, prosthetic tissue valves and/or annular ring and/or structural ring formed therefrom) further comprises at least one additional biologically active agent or composition, i.e., an agent that induces or modulates a physiological or biological process, or cellular activity, e.g., induces proliferation, and/or growth and/or regeneration of tissue.

According to the invention, suitable biologically active agents include any of the aforementioned biologically active agents, including, without limitation, the aforementioned growth factors, cells and proteins.

In some embodiments of the invention, the ECM composition (and, hence, prosthetic tissue valves and/or annular ring and/or structural ring formed therefrom) further comprises at least one pharmacological agent or composition (or drug), i.e., an agent or composition that is capable of producing a desired biological effect in vivo, e.g., stimulation or suppression of apoptosis, stimulation or suppression of an immune response, etc.

According to the invention, suitable pharmacological agents and compositions include any of the aforementioned agents, including, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombotic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the pharmacological agent comprises an anti-inflammatory agent.

In some embodiments, the pharmacological agent comprises a statin, i.e., a HMG-CoA reductase inhibitor. According to an aspect of the invention, suitable statins include, without limitation, atorvastatin (Lipitor®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Crestor®), and simvastatin (Zocor®, Lipex®). Several actives comprising a combination of a statin and another agent, such as ezetimbe/simvastatin (Vytorin®), are also suitable.

It has been found that the noted statins exhibit numerous beneficial properties that provide several beneficial biochemical actions or activities in vivo; particularly, when the statins are a component of an ECM composition comprising acellular ECM, i.e., a statin augmented ECM composition. The properties and beneficial actions are set forth in Applicant's U.S. Pat. No. 9,072,816 and U.S. application. Ser. No. 13/782,024, filed on Mar. 1, 2013 and Ser. No. 14/554,730, filed on Nov. 26, 2014; which are incorporated by reference herein in their entirety.

In some embodiments of the invention, the pharmacological agent comprises chitosan. As also set forth in detail in U.S. Pat. No. 9,072,816, chitosan similarly exhibits numerous beneficial properties that provide several beneficial biochemical actions or activities in vivo; particularly when chitosan is a component of an ECM composition comprising acellular ECM.

As indicated above, it is contemplated that, following placement of an ECM prosthetic tissue valve of the invention on a cardiovascular structure (or structures) in a subject, e.g., valve annulus, and, hence, cardiovascular tissue associated therewith, the ECM prosthetic tissue valve will induce "modulated healing" of the cardiovascular structure (s) and cardiovascular tissue associated therewith.

The term "modulated healing", as used herein, and variants of this language generally refer to the modulation (e.g., alteration, delay, retardation, reduction, etc.) of a process involving different cascades or sequences of naturally occurring tissue repair in response to localized tissue damage or injury, substantially reducing their inflammatory effect. Modulated healing, as used herein, includes many different biologic processes, including epithelial growth, fibrin deposition, platelet activation and attachment, inhibition, proliferation and/or differentiation, connective fibrous tissue production and function, angiogenesis, and several stages of acute and/or chronic inflammation, and their interplay with each other.

For example, in some embodiments of the invention, the ECM prosthetic tissue valves of the invention are specifically formulated (or designed) to alter, delay, retard, reduce, and/or detain one or more of the phases associated with healing of damaged tissue, including, but not limited to, the inflammatory phase (e.g., platelet or fibrin deposition), and the proliferative phase when in contact with biological tissue.

In some embodiments, "modulated healing" means and includes the ability of an ECM prosthetic tissue valve of the invention to restrict the expression of inflammatory components. By way of example, according to the invention, when a tubular member or conical shaped member (and/or annular ring and/or structural ring) of a prosthetic tissue valve comprises a statin augmented ECM composition, i.e., a composition comprising ECM and a statin, and the ECM prosthetic tissue valve is positioned proximate damaged biological tissue, e.g., attached to a valve annulus, the ECM prosthetic tissue valve restricts expression of monocyte chemoattractant protein-1 (MCP-1) and chemokine (C—C) motif ligand 2 (CCR2).

In some embodiments of the invention, "modulated healing" means and includes the ability of an ECM prosthetic tissue valve of the invention to alter a substantial inflammatory phase (e.g., platelet or fibrin deposition) at the beginning of the tissue healing process. As used herein, the phrase "alter a substantial inflammatory phase" refers to the ability of a prosthetic tissue valve of the invention to substantially reduce the inflammatory response at a damaged tissue site, e.g., valve annulus, when in contact with tissue at the site.

In such an instance, a minor amount of inflammation may ensue in response to tissue injury, but this level of inflammation response, e.g., platelet and/or fibrin deposition, is substantially reduced when compared to inflammation that takes place in the absence of an ECM prosthetic tissue valve of the invention.

The term "modulated healing" also refers to the ability of an ECM prosthetic tissue valve of the invention to induce host tissue proliferation, bioremodeling, including neovascularization, e.g., vasculogenesis, angiogenesis, and intussusception, and regeneration of tissue structures with site-specific structural and functional properties, when disposed proximate damaged tissue, e.g., valve annulus.

Thus, in some embodiments of the invention, the term "modulated healing" means and includes the ability of an ECM prosthetic tissue valve of the invention to modulate inflammation and induce host tissue proliferation and remodeling, when disposed proximate damaged tissue.

It is further contemplated that, during a cardiac cycle after placement of an ECM prosthetic tissue valve on a valve structure or structures, wherein the ECM prosthetic tissue valve is subjected to physical stimuli, adaptive regeneration of the prosthetic tissue valve is also induced.

By the term "adaptive regeneration," it is meant to mean the process of inducing modulated healing of damaged tissue concomitantly with stress-induced hypertrophy of an ECM prosthetic tissue valve of the invention, wherein the ECM prosthetic tissue valve adaptively remodels and forms functioning valve structures that are substantially identical to native valve structures.

As indicated above, it is further contemplated that the points at which an ECM prosthetic tissue valve is attached to a cardiovascular structure (or structures) in a subject will serve as points of constraint that direct the remodeling of the ECM into cardiovascular tissue and valve structures that are substantially identical to properly functioning native cardiovascular tissue and valve structures.

Referring now to FIGS. 2-5, two (2) embodiments of prosthetic tissue valves of the invention will be described in detail.

Figure 2:
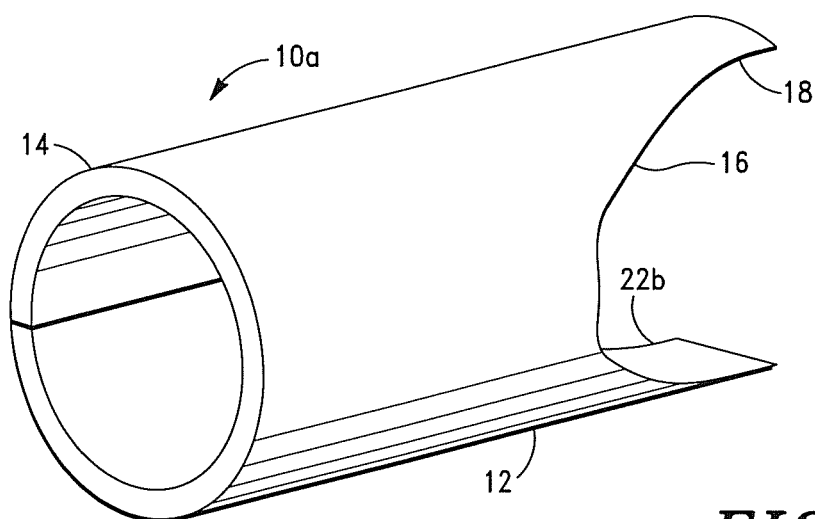
FIG. 2 is a perspective view of one embodiment of a prosthetic tissue valve, in accordance with the invention.
Figure 3:
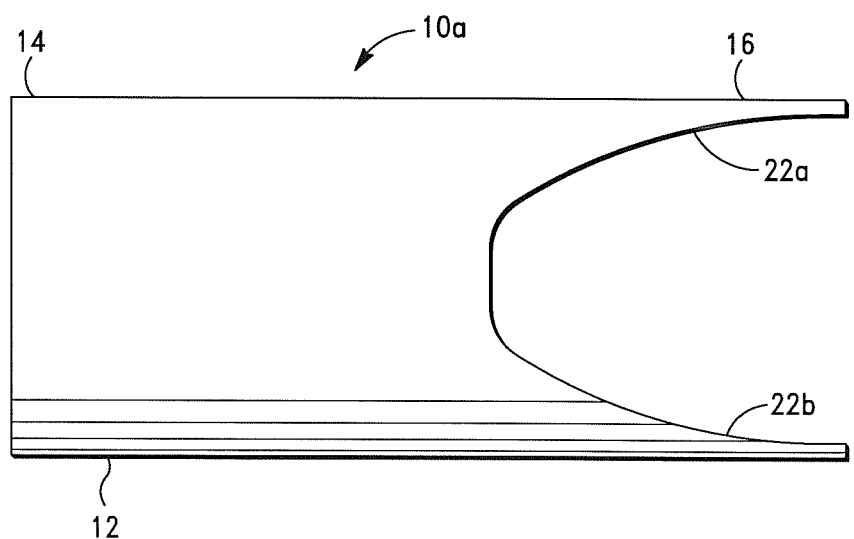
FIG. 3 is a side plane view of the prosthetic tissue valve shown in FIG. 2, in accordance with the invention.

Referring first to FIGS. 2 and 3, in one embodiment of the invention, the prosthetic tissue valve 10a comprises a continuous tubular member 12 having first or "proximal" and second or "distal" ends 14, 16. In some embodiments of the invention, the valve 10a further comprises at least one internal leaflet, such as disclosed in U.S. Pat. No. 8,709,076 and U.S. application Ser. No. 13/804,683, which are incorporated by reference herein.

In some embodiments, the tubular member 12 comprises a leaflet forming interior surface, such as disclosed in U.S. application Ser. Nos. 13/480,324 and 13/480,347, now U.S. Pat. Nos. 8,696,744 and 8,845,719, which are similarly incorporated by reference herein.

According to the invention, the tubular member 12 can comprise various biocompatible materials, including, without limitation, mammalian tissue, e.g., bovine tissue.

As indicated above, in a preferred embodiment, the tubular member 12 comprises an ECM composition comprising acellular ECM from a mammalian tissue source.

In some embodiments of the invention, the tubular member 12 comprises a polymer composition comprising a biocompatible polymeric material. According to the invention, suitable polymeric materials comprise Dacron®, polyether ether ketone (PEEK), and like materials.

In a preferred embodiment of the invention, the distal end 16 of the tubular member 12 includes cardiovascular structure engagement means 18 that is designed and configured to securely engage the tubular member 12 and, hence, prosthetic tissue valve 10a formed therefrom, to cardiovascular structures, such as selective papillary muscles and/or cardiovascular tissue.

As illustrated in FIGS. 2 and 3, in some embodiments of the invention, the cardiovascular structure engagement means 18 comprises a pair of valve leaflet extensions 22a, 22b, which, in some embodiments of the invention, extend from a valve leaflet to mimic the chordae tendineae. According to the invention, the valve leaflet extensions 22a, 22b can be disposed at various positions about the periphery of the distal end 16 of the tubular member 12.

In some embodiments of the invention, wherein the prosthetic tissue valve 10a is employed to replace a mitral valve, the leaflet extensions 22a, 22b are preferably spaced at approximately 0° and 120° about the periphery of the distal end 16 of the tubular member 12.

According to the invention, the valve leaflet extensions 22a, 22b can also have various predetermined lengths to accommodate attachment to desired cardiovascular structures, e.g., selective papillary muscles.

The valve leaflet extensions 22a, 22b can also comprise the same material as the tubular member 12 or a different material, e.g., tubular member 12 comprises SIS and the valve leaflet extensions 22a, 22b comprise a polymeric material.

Figure 4:
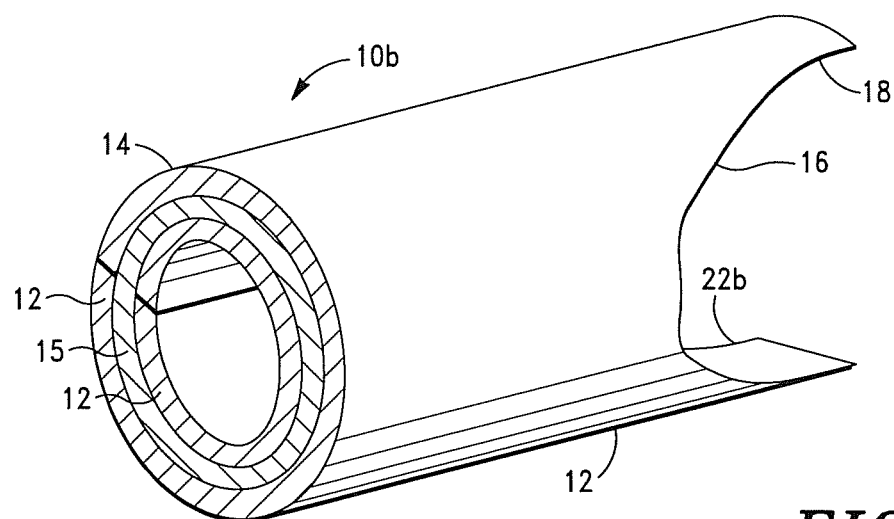
FIG. 4 is a perspective partial sectional view of another embodiment of a prosthetic tissue valve shown in FIG. 2 having an annular ring disposed at the proximal end of the valve, in accordance with the invention.
Figure 5:
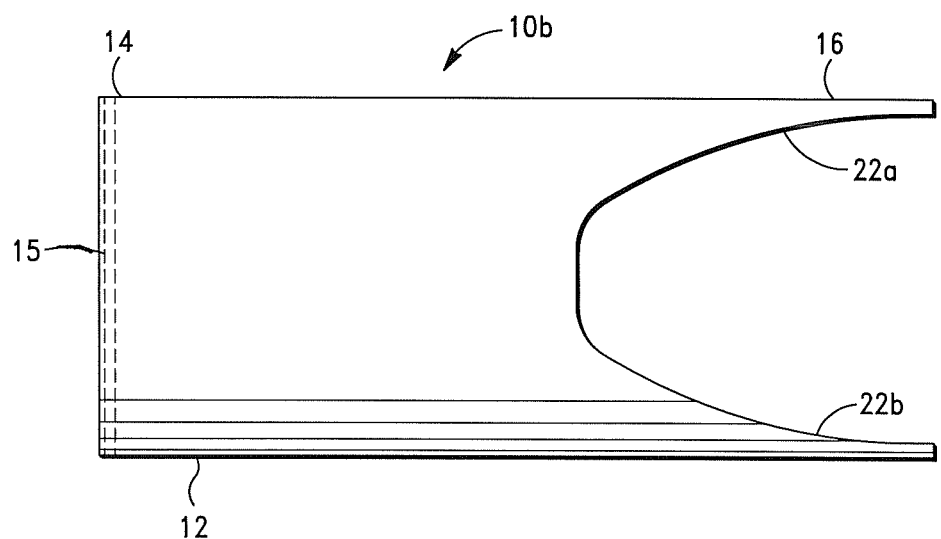
FIG. 5 is a side plane view of the prosthetic tissue valve shown in FIG. 4, in accordance with the invention.

Referring now to FIGS. 4 and, 5, in a further embodiment of the invention, the prosthetic tissue valve 10a shown in FIGS. 2 and 3 further comprises an annular ring 15 that is disposed on the proximal end 14 of the valve 10a, forming valve 10b. As indicated above, suitable annular rings and ring materials are disclosed in U.S. application Ser. No. 14/953,548.

Figure 6:
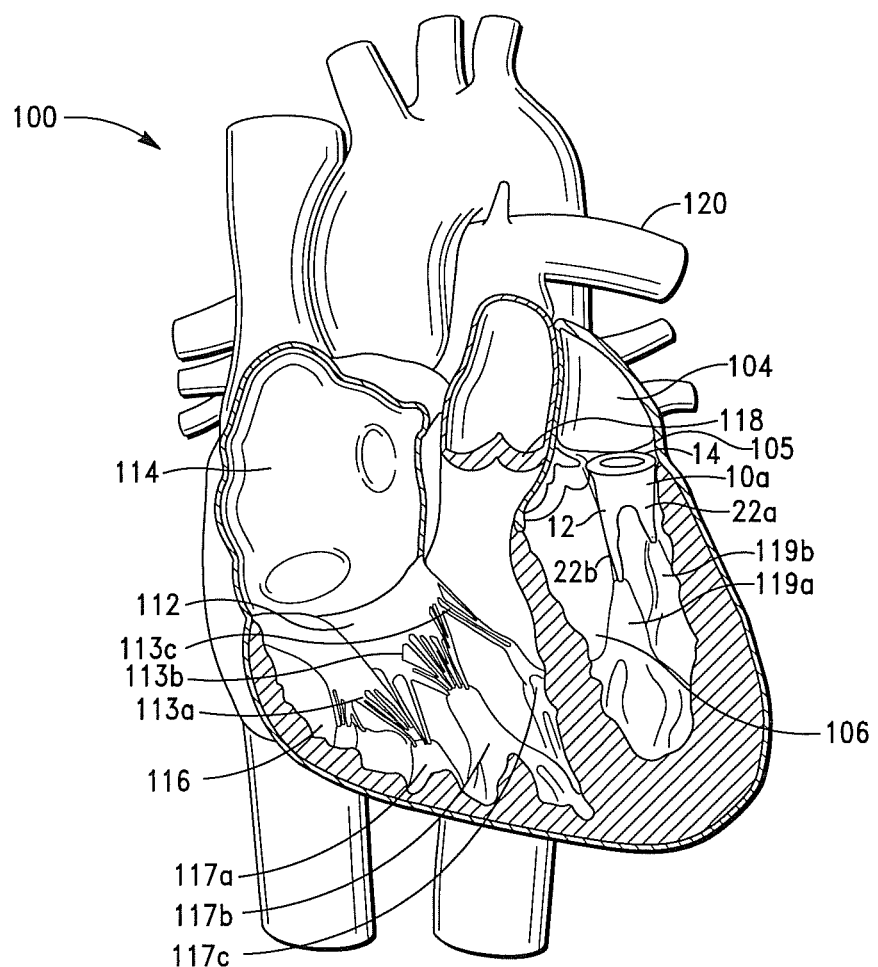
FIG. 6 is an illustration of the prosthetic tissue valve shown in FIG. 4 secured to the mitral valve annulus region and papillary muscles, in accordance with the invention.

Referring now to FIG. 6, placement of prosthetic tissue valve 10a proximate a mitral valve region will be described in detail.

According to the invention, the prosthetic tissue valve 10a is disposed proximate the mitral valve region. The initial placement of the valve 10a can be achieved by various conventional means, including limited access heart surgery and percutaneous delivery.

The proximal end 14 of the valve 10a is then sutured to the mitral valve annulus 105. The valve leaflet extensions 22a, 22b are then attached directly to the papillary muscles 119a, 119b.

It is contemplated that, following attachment of the valve leaflet extensions 22a, 22b to the papillary muscles 119a, 119b, the valve leaflet extensions 22a, 22b fuse to the papillary muscles 119a, 119b and, in some embodiments, the valve leaflet extensions 22a, 22b remodel and regenerate functioning native chordae tendineae.

As indicated above, when the prosthetic tissue valve 10a (and prosthetic tissue valve 10b) comprises an ECM prosthetic tissue valve, it is also contemplated that the points at which the valve leaflet extensions 22a, 22b connect to the papillary muscles 119a, 119b and the proximal end 14 of the valve 12 is attached to the mitral valve annulus 105 will serve as points of constraint that direct the remodeling of the prosthetic tissue valve 10a (and prosthetic tissue valve 10b) into valve tissue and/or valve structures, including chordae tendineae, that are identical or substantially identical to properly functioning native valve tissue and valve structures.

According to the invention, the valve leaflet extensions 22a, 22b and noted placement and attachment thereof significantly enhances the strength and, hence, structural integrity of prosthetic tissue valves 10a, 10b shown in FIGS. 2-5. The valve leaflet extensions 22a, 22b and noted placement and attachment thereof also preserves the structural integrity of the papillary muscles 119a, 119b.

The valve leaflet extensions 22a, 22b (and noted placement and attachment thereof) thus significantly reduces the risk of suture failure and rupture of the prosthetic valve tissue proximate the papillary muscles 119a, 119b. The valve leaflet extensions 22a, 22b (and noted placement and attachment thereof) also significantly reduce the risk of rupture of the papillary muscles 119a, 119b.

Figure 7A:
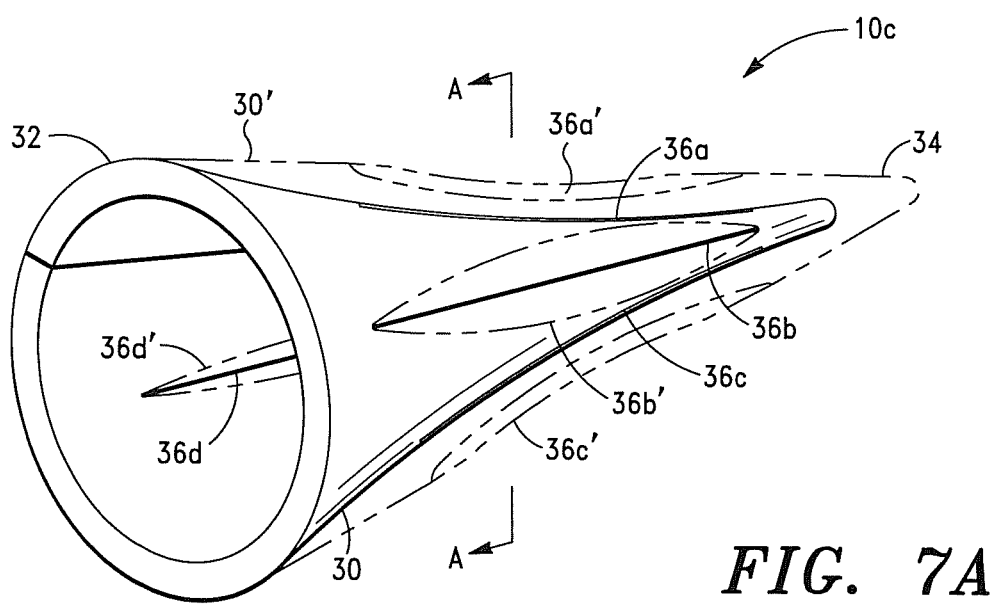
FIG. 7A is a perspective view of another embodiment of a prosthetic tissue valve, in accordance with the invention.
Figure 7B:
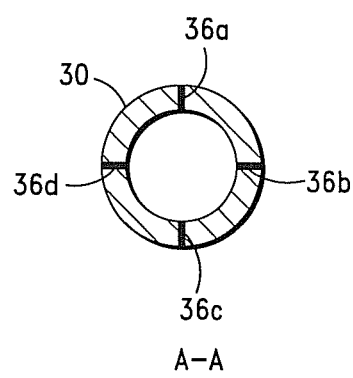
FIG. 7B is an end plane view of the prosthetic tissue valve shown in FIG. 7A, in accordance with the invention.

Referring now to FIGS. 7A and 7B, there is shown another embodiment of a prosthetic tissue valve of the invention (denoted "10c"). As illustrated in FIG. 7A, the prosthetic tissue valve 10c comprises a continuous conical shaped member 30.

As illustrated in FIG. 7A, the prosthetic tissue valve 10c further comprises proximal and distal ends 32, 34. According to the invention, the proximal end 32 of the valve 10c is sized and configured to engage a valve annulus region of a mammalian heart.

In some embodiments of the invention, the proximal end 32 of the prosthetic tissue valve 10c (and prosthetic tissue valves 10d and 10e, discussed below) has an outer diameter in the range of approximately 1.0 mm to 5 cm.

According to the invention, the conical shaped member 30 and, hence, prosthetic tissue valve 10c can (and prosthetic tissue valves 10d-10e) comprise any length. In some embodiments of the invention, the prosthetic tissue valve 10c (and prosthetic tissue valves 10d-10e) has a length in the range of approximately 5 mm to 150 mm.

In some embodiments of the invention, the conical shaped member 30 and, hence, prosthetic tissue valve 10c (and prosthetic tissue valves 10d-10e) has a proximal end diameter and length ratio in the range of 5:1 to 2:1.

As illustrated in FIGS. 7A and 7B, the prosthetic tissue valve 10c further comprises a plurality of open regions 36a-36d that are preferably disposed linearly (i.e., parallel to the longitudinal axis of the valve 10c) over a portion of the length of the member 30. According to the invention, the length and width of the open regions 36a-36d can comprise any length or width.

In some embodiments of the invention, the open regions 36a-36d have a length that is in the range of approximately 10% to 98% of the overall length of the conical shaped member 30.

In some embodiments, the width of the open regions 36a-36d is in the range of approximately 1 mm to 30 mm.

According to the invention, the open regions 36a-36d can have the same length and width or different lengths and widths. In some embodiments of the invention, the open regions 36a-36d have the same length and width.

Figure 7C:
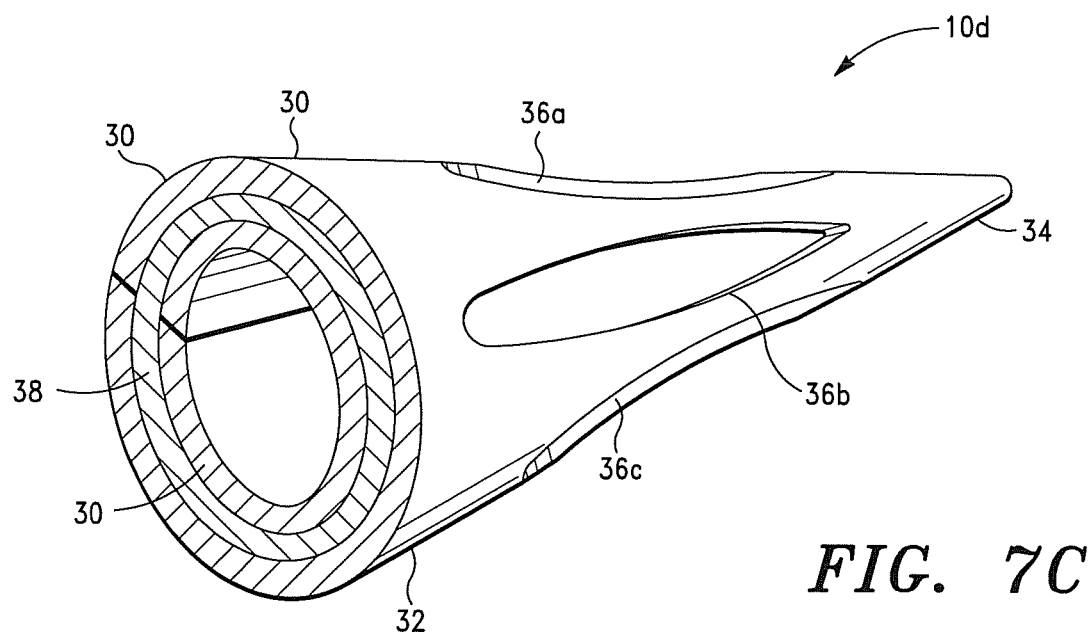
FIG. 7C is a perspective view partial sectional of another embodiment of the prosthetic tissue valve shown in FIG. 7A having an annular ring disposed at the proximal end of the valve, in accordance with the invention.

Referring now to FIG. 7C, there is shown another embodiment of the prosthetic tissue valve 10c that is shown in FIG. 7A. As illustrated in FIG. 7C, the prosthetic tissue valve, now denoted 10d, further comprises an annular ring 38 that is designed and configured to securely engage the prosthetic tissue valve 10d to a valve annulus (and, hence, cardiovascular tissue associated therewith).

According to the invention, the outer circumference of the annular ring 38 can comprise various dimensions. In some embodiments of the invention, the ratio of the circumference of the annular ring 38 to the operative valve circumference of prosthetic tissue valve 10c (and prosthetic tissue valves 10d-10h) is in the range of approximately 1:1 to approximately 3:1.

Figure 7D:
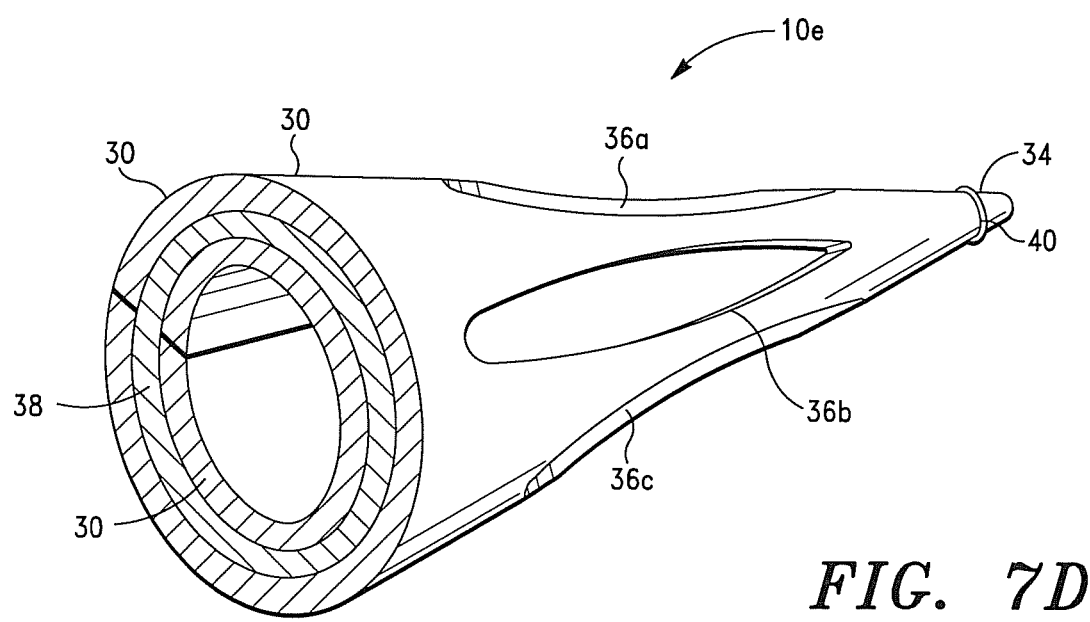
FIG. 7D is a perspective view partial sectional of yet another embodiment of the prosthetic tissue valve shown in FIG. 7A having an annular ring disposed at the proximal end of the valve and a structural ring disposed at the distal end of the valve, in accordance with the invention.

Referring now to FIG. 7D, there is shown yet another embodiment of the prosthetic tissue valve 10c that is shown in FIG. 7A. As illustrated in FIG. 7D, the prosthetic tissue valve, now denoted 10e, further comprises a structural ring 40 that is disposed on the distal end 34 of the valve 10e.

As indicated above, according to the invention, the annular ring 38 and/or structural ring 40 can comprise various biocompatible materials, such as disclosed in U.S. application Ser. No. 14/953,548.

Figure 8A:
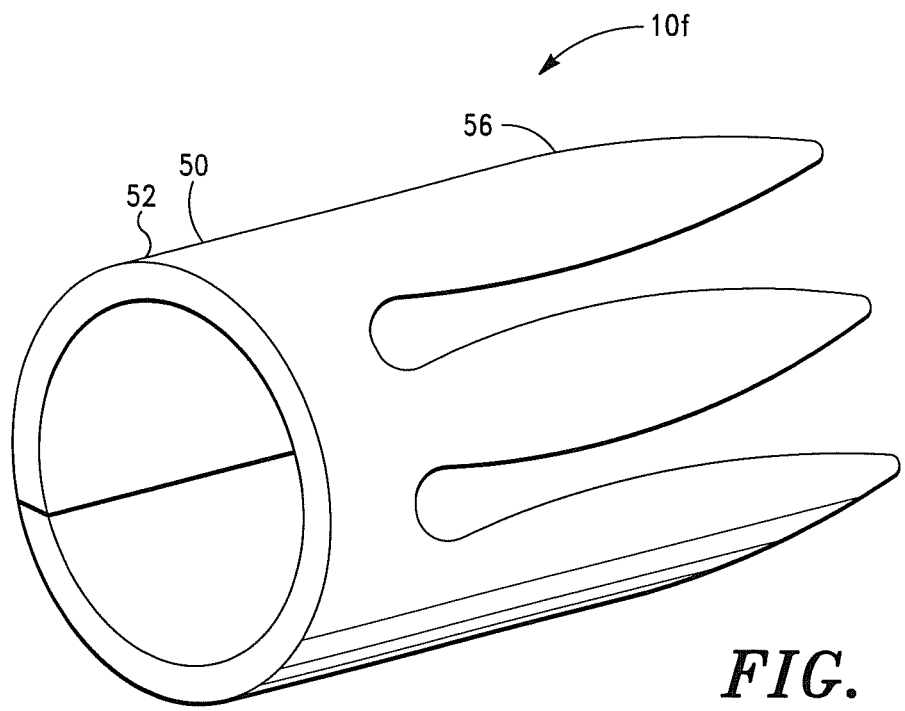
FIG. 8A is a perspective view of another embodiment of a prosthetic tissue valve, in accordance with the invention.
Figure 8B:
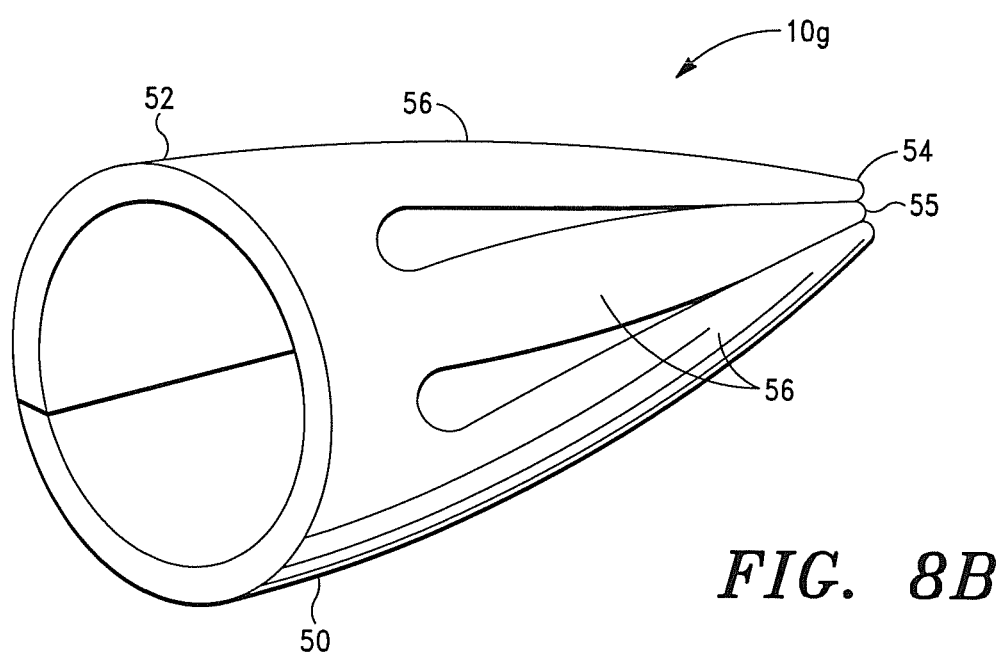
FIG. 8B is a perspective view of another embodiment of a prosthetic tissue valve, in accordance with the invention.

Referring now to FIGS. 8A and 8B there are shown further embodiments of prosthetic tissue valves of the invention, where FIG. 8A illustrates a prosthetic tissue valve, denoted 10f, having a tubular structure and FIG. 8B illustrates a prosthetic tissue valve, denoted 10g, having a conical shaped structure.

As illustrated in FIGS. 8A and 8B, in a preferred embodiment of the invention, the prosthetic tissue valves 10f, 10g comprise a base member 50 having a plurality of ribbons 56 that extend from the proximal end 52 to the distal end 54 of the base member 50.

According to the invention, the base member 50 can comprise any number of ribbons 56. In some embodiments of the invention, the base member 50 has four (4) equally spaced ribbons 56.

According to the invention, the proximal end 52 of the prosthetic tissue valves 10f, 10g is similarly sized and configured to engage an annular region of a mammalian heart.

According to the invention, the proximal end 52 of the prosthetic tissue valves 10f, 10g (and prosthetic tissue valves 10h and 10i, discussed below) can similarly comprise a circumference, i.e., operative valve circumference, in the range of approximately 20 mm to 220 mm.

According to the invention, the prosthetic tissue valves 10f, 10g (and prosthetic tissue valves 10h and 10i) can also comprise any length. In some embodiments of the invention, the prosthetic tissue valves 10f, 10g (and prosthetic tissue valves 10h and 10i) have a length in the range of approximately 10 mm to 100 mm.

In some embodiments of the invention, the prosthetic tissue valves 10f, 10g (and prosthetic tissue valves 10h and 10i) have a proximal end diameter and length ratio in the range of 5:1 to 2:1.

Figure 8C:
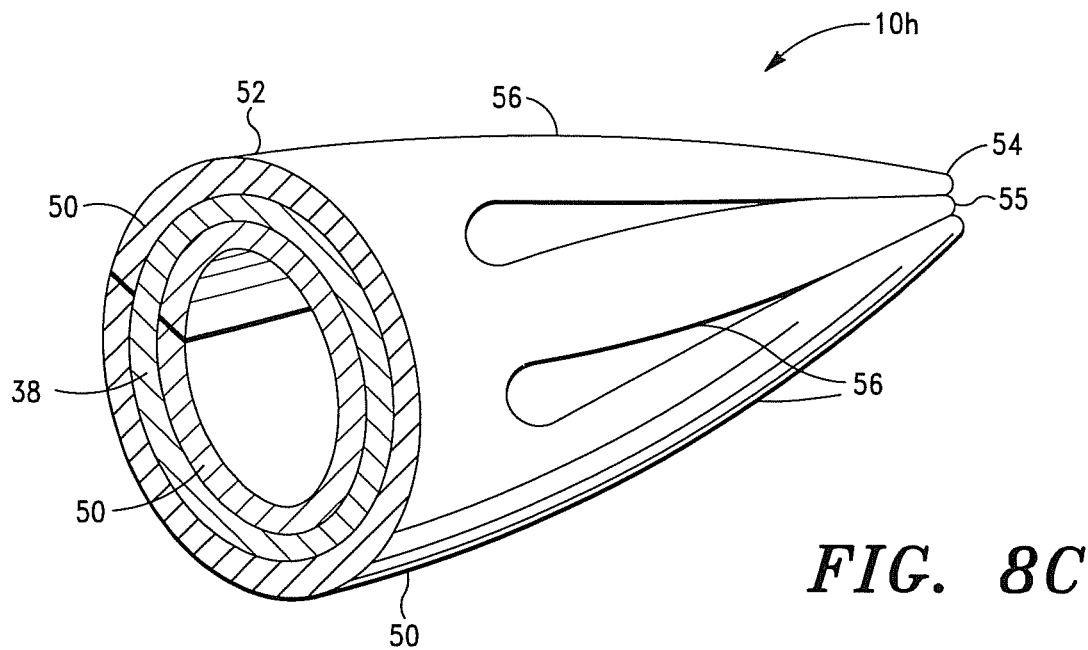
FIG. 8C is a perspective partial sectional view of another embodiment of the prosthetic tissue valve shown in FIG. 8B having an annular ring disposed at the proximal end of the valve, in accordance with the invention.

Referring now to FIG. 8C, there is shown another embodiment of the prosthetic tissue valve 10g that is shown in FIG. 8B. As illustrated in FIG. 8C, the prosthetic tissue valve, now denoted 10h, similarly comprises annular ring 38, which is designed and configured to securely engage the valve 10h to a valve annulus (and, hence, cardiovascular tissue associated therewith).

Figure 8D:
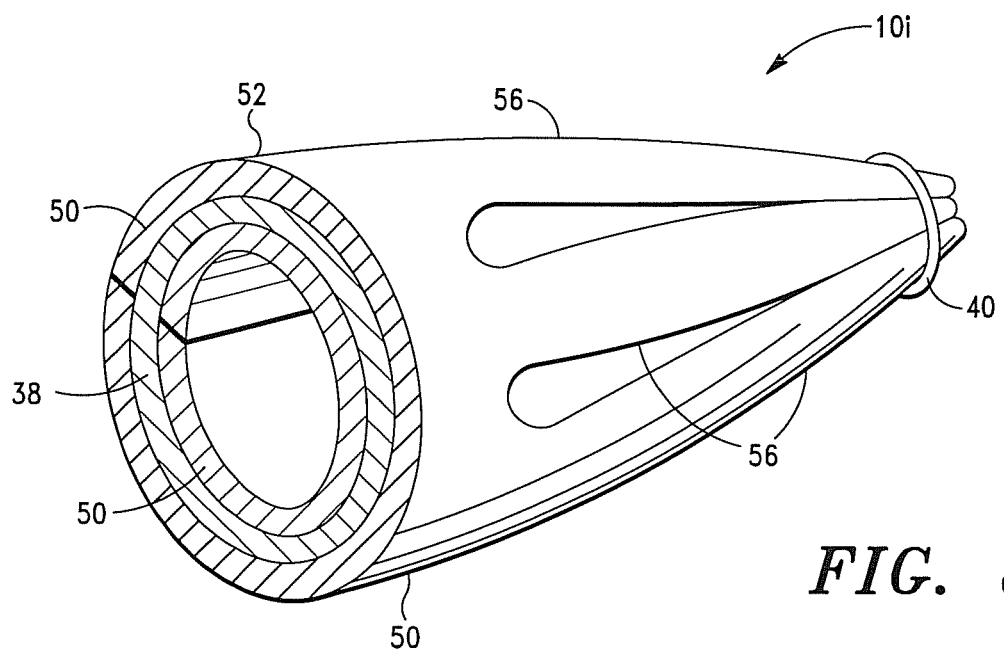
FIG. 8D is a perspective partial sectional view of yet another embodiment of the prosthetic tissue valve shown in FIG. 8B having an annular ring disposed at the proximal end of the valve and a structural ring disposed at the distal end of the valve, in accordance with the invention.

Referring now to FIG. 8D, there is shown yet another embodiment of the prosthetic tissue valve 10g that is shown in FIG. 8B. As illustrated in FIG. 8D, the prosthetic tissue valve, now denoted 10i, further comprises a structural ring 40 that is disposed on the distal end 54 of the valve 10i.

According to the invention, the structural ring 40 is preferably sized and configured to receive ribbons 56 therein in close proximity to each other, as shown in FIG. 8D.

According to the invention, the proximal end of the prosthetic tissue valves of the invention can be secured to a valve annulus by various conventional means, such as suturing the proximal end (with or without an annular ring 38) directly to the valve annulus tissue.

In some embodiments of the invention, ribbons 56 of prosthetic tissue valves 10f, 10g, 10h and 10i are connected via a constraining band that is positioned between the proximal and distal ends 52, 54 of the valves 10f, 10g, 10h and 10i.

In some embodiments of the invention, ribbons 56 of prosthetic tissue valves 10f, 10g, 10h and 10i are restrained at a predetermined valve region, e.g., mid-point, between the proximal and distal ends 52, 54 of the valves 10f, 10g, 10h, 10i via a supplemental structural ring.

In some embodiments of the invention, the base member 50 (and, hence, ribbons 56) of prosthetic tissue valves 10f, 10g, 10h and 10i comprise an outer coating.

In some embodiments of the invention, the coating comprises an ECM composition comprising acellular ECM from one of the aforementioned mammalian tissue sources.

In some embodiments, the ECM composition further comprises at least one of the aforementioned biologically active agents or compositions.

In some embodiments, the ECM composition further comprises at least one of the aforementioned pharmacological agents or compositions.

In some embodiments of the invention, the coating comprises one of the aforementioned polymeric compositions.

Figure 9:
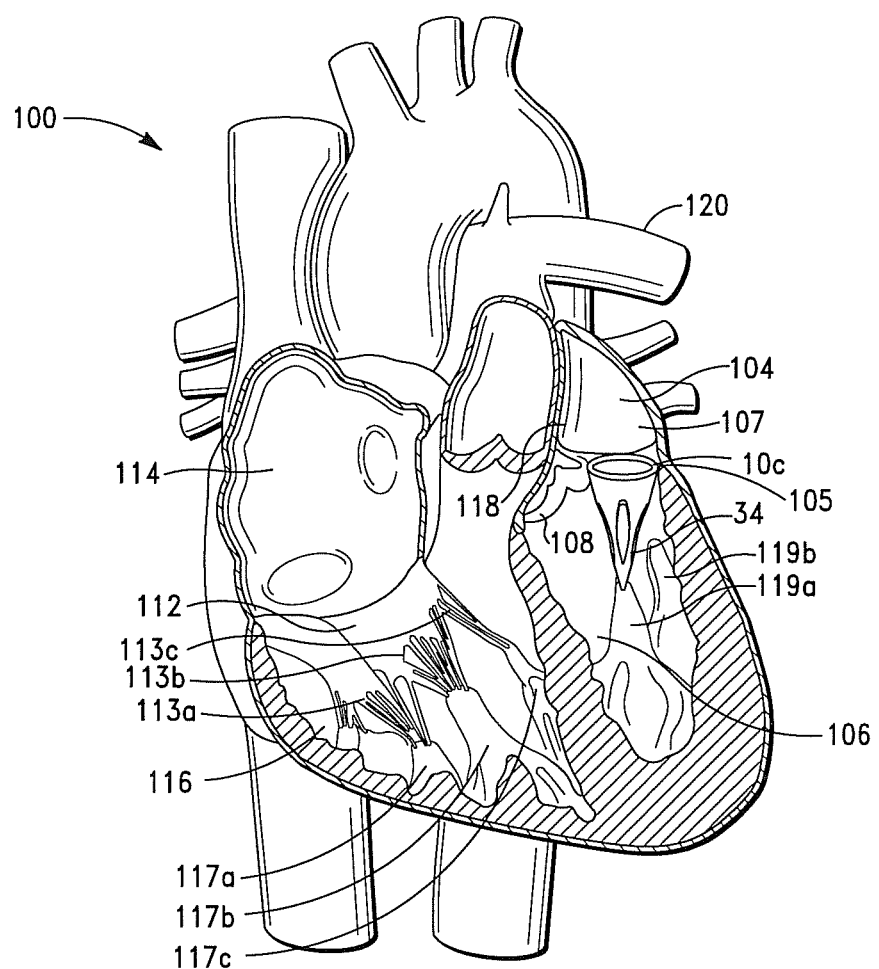
FIG. 9 is an illustration of the prosthetic tissue valve shown in FIG. 7A secured to the mitral valve annulus region, in accordance with the invention.

Referring now to FIG. 9, placement of prosthetic tissue valve 10c in a mitral valve region will now be described in detail.

According to the invention, prior to placement of prosthetic tissue valve 10c (as well as prosthetic tissue valves 10d and 10e and prosthetic tissue valves 10f-10i) in a mitral valve region, the mitral valve 102 and chordae tendineae 103a, 103b can be removed or retained. Thus, in some embodiments of the invention, the mitral valve 102 and chordae tendineae 103a, 103b are retained. In some embodiments, the mitral valve 102 and chordae tendineae 103a, 103b are removed.

After the mitral valve annulus region 107 is prepared, and, if elected, the mitral valve 102 and chordae tendineae 103a, 103b are removed, the prosthetic tissue valve 10c is disposed proximate the mitral valve annulus region 107.

According to the invention, the initial placement of prosthetic tissue valve 10c (as well as prosthetic tissue valves 10d and 10e and prosthetic tissue valves 10f-10i) can be achieved by various conventional means, including limited access heart surgery and percutaneous transatrial, i.e., through the left atrium, and transapical delivery.

After disposing prosthetic tissue valve 10c proximate the mitral valve region 107, the proximal end 32 of prosthetic tissue valve 10c is secured to the mitral valve annulus 105.

In some embodiments of the invention, the distal end 34 of prosthetic tissue valve 10c is secured to a papillary muscle, in this instance papillary muscle 119a, as illustrated in FIG. 9.

Figure 10:
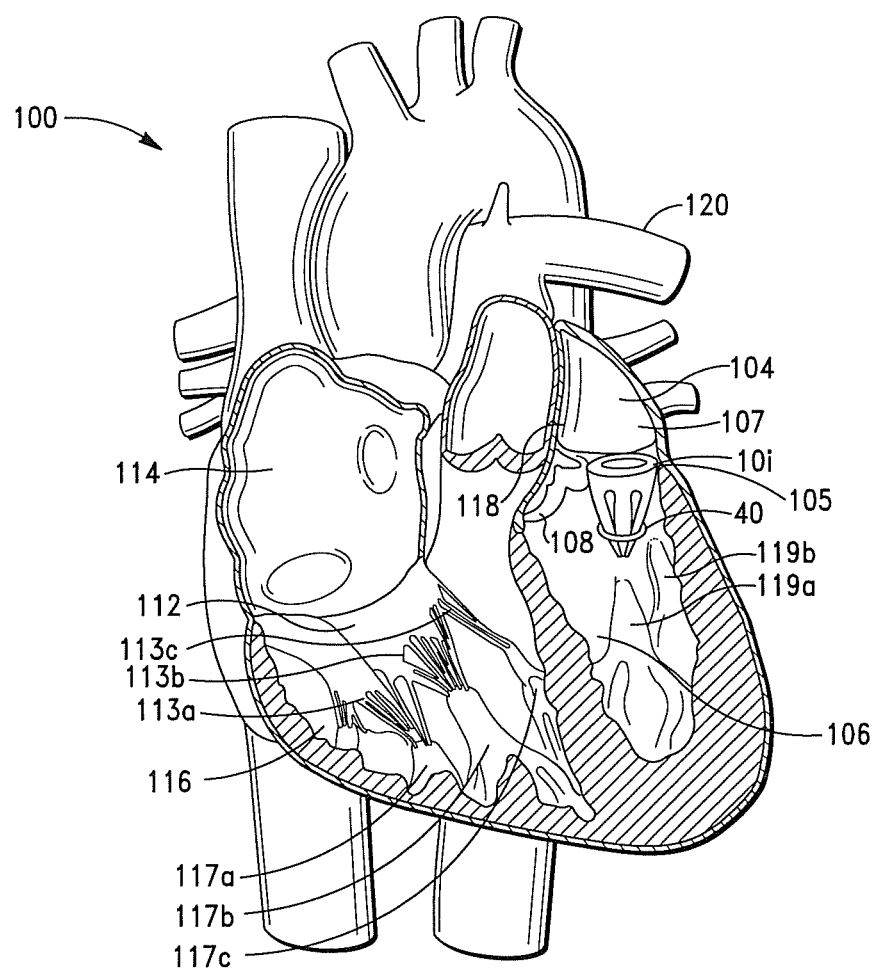
FIG. 10 is an illustration of the prosthetic tissue valve shown in FIG. 8D secured to the mitral valve annulus region, in accordance with the invention.

Referring now to FIG. 10, placement of prosthetic tissue valve 10i in a mitral valve region will now be described in detail.

After the mitral valve annulus region 107 is prepared and, if elected, the mitral valve 102 and chordae tendineae 103a, 103b are removed, prosthetic tissue valve 10i is similarly disposed proximate the mitral valve annulus region 107. The proximal end 32 of prosthetic tissue valve 10i is then secured to the mitral valve annulus 105.

According to the invention, the distal ends 54 of the ribbons 56 of prosthetic tissue valve 10i can also be secured to one or more papillary muscles, e.g., papillary muscles 119a, 119b, such as prosthetic tissue valve 10a shown in FIG. 6.

Figure 11:
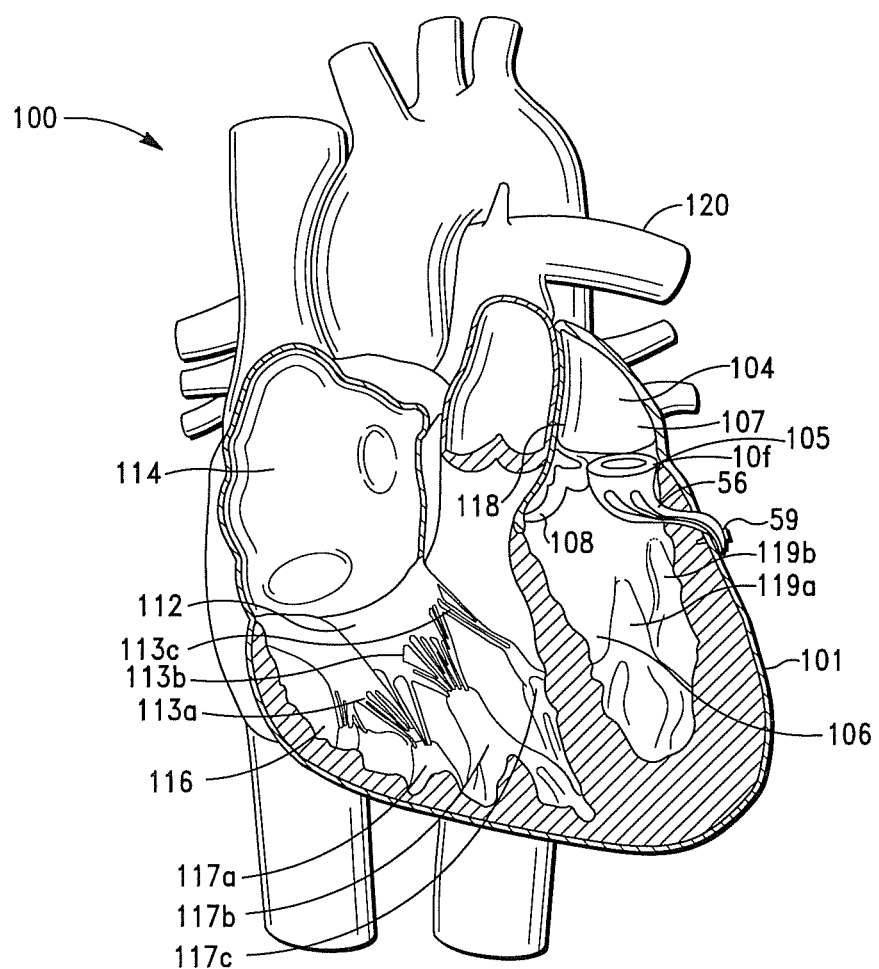
FIG. 11 is an illustration of the prosthetic tissue valve shown in FIG. 8A secured to the mitral valve annulus region, in accordance with the invention.

Referring now to FIG. 11, placement of prosthetic tissue valve 10f in a mitral valve region will now be described in detail.

After the mitral valve annulus region 107 is prepared and, if elected, the mitral valve 102 and chordae tendineae 103a, 103b are removed, prosthetic tissue valve 10f is similarly disposed proximate the mitral valve annulus region 107. The proximal end 52 of prosthetic tissue valve 10i is then secured to the mitral valve annulus 105.

According to the invention, the distal ends 54 of the ribbons 56 of prosthetic tissue valve 10f can then be connected to the inner surface of the ventricle 106 via at least one active fixation lead (not shown), one or more papillary muscles, such as prosthetic tissue valve 10a shown in FIG. 6, or, as illustrated in FIG. 11, threaded through the heart wall 101 and attached on the outside of the heart 100 via a cork-screw mechanism 59.

In some embodiments of the invention, the prosthetic tissue valves of the invention further comprise a supplemental support structure. In some embodiments, the support structure comprises at least one internal biocompatible support ring that is disposed between the proximal and distal end of the valves. In some embodiments, the support structure comprises a biocompatible multi-link stent structure.

In some embodiments of the invention, the prosthetic tissue valves of the invention further comprise at least one internal pre-formed leaflet, such as disclosed in Applicant's U.S. Pat. Nos. 8,709,076, 9,011,526, 8,257,434 and 7,998,196, which are incorporated by reference herein.

As indicated above, it is contemplated that, when the prosthetic tissue valves described herein comprise an ECM composition comprising acellular ECM (i.e., ECM prosthetic tissue valves 10a-10i), upon placement of ECM prosthetic tissue valves 10a-10i proximate to a valve structure, e.g., mitral valve annulus 105, modulated healing of the valve structure and connecting cardiovascular structure tissue will be effectuated.

It is further contemplated that, following placement of ECM prosthetic tissue valves 10a-10i in a subject on a cardiovascular structure (or structures) in a subject, the ECM prosthetic tissue valves 10a-10i will become populated with cells from the subject that will gradually remodel the ECM into cardiovascular tissue and tissue (and, hence, valve) structures.

It is further contemplated that, following placement of ECM prosthetic tissue valves 10a-10i in a subject on a cardiovascular structure (or structures) in a subject, stem cells will migrate to the ECM prosthetic tissue valves 10a-10i from the point(s) at which the valves 10a-10i are attached to the cardiovascular structure, e.g., mitral valve annulus 105, or structures, e.g., valve annulus and heart wall.

It is still further contemplated that the points at which the ECM prosthetic tissue valves 10a-10i are attached to a cardiovascular structure (or structures) in a subject will serve as points of constraint that direct the remodeling of the ECM into cardiovascular tissue and valve structures that are identical or substantially identical to properly functioning native cardiovascular tissue and valve structures.

It is still further contemplated that, during circulation of epithelial and endothelial progenitor cells after placement of the ECM prosthetic tissue valves 10a-10i on a cardiovascular structure (or structures), the surfaces of the ECM prosthetic tissue valves 10a-10i will rapidly become lined or covered with epithelial and/or endothelial progenitor cells.

As will readily be appreciated by one having ordinary skill in the art, the present invention provides numerous advantages compared to prior art prosthetic valves. Among the advantages are the following:

The provision of improved prosthetic xenograft tissue valves with minimal in vivo calcification and cytotoxicity, and optimum blood flow modulation and characteristics The provision of improved prosthetic xenograft tissue valves and methods for attaching same to cardiovascular structures and/or tissue.

The provision of improved prosthetic xenograft tissue valves and methods for attaching same to cardiovascular structures and/or tissue that preserve the structural integrity of the cardiovascular structure(s) when attached thereto;

The provision of prosthetic xenograft tissue valves that induce modulated healing, including host tissue proliferation, bioremodeling and regeneration of new tissue and tissue structures with site-specific structural and functional properties;

The provision of prosthetic xenograft tissue valves that induce adaptive regeneration;

The provision of prosthetic xenograft tissue valves that are capable of administering a pharmacological agent to host tissue and, thereby produce a desired biological and/or therapeutic effect;

The provision of prosthetic xenograft valves that can be implanted without removal of the native AV valve;

The provision of prosthetic xenograft valves that can be implanted without a cardiopulmonary bypass apparatus;

The provision of prosthetic xenograft valves that can be positioned proximate a valve annulus transvascularly; and The provision of prosthetic xenograft valves that can be positioned proximate a valve annulus transapically.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A prosthetic valve for modulating fluid flow through an atrioventricular (AV) valve annulus region during cardiac cycles of a heart, said fluid flow exhibiting a plurality of positive and negative flow pressures during said cardiac cycles, said prosthetic valve comprising:

a remodelable biological tissue structure, said remodelable biological tissue structure defining a continuous tubular shaped sheet member, said tubular shaped sheet member comprising an adaptive regeneration system adapted to induce modulated healing of cardiovascular tissue of said AV valve annulus region concomitantly with stress-induced hypertrophy of said tubular shaped sheet member when said tubular shaped sheet member is subjected to cardiac cycle induced physical stimuli, said modulated healing of said damaged cardiovascular tissue comprising inflammation modulation of said damaged cardiovascular tissue and induced neovascularization, remodeling of said damaged cardiovascular tissue and regeneration of new cardiovascular tissue and tissue structures with site-specific structural and functional properties, said stress-induced hypertrophy of said tubular shaped sheet member comprising adaptive remodeling of said tubular shaped sheet member, wherein said tubular shaped sheet member remodels and forms functioning valve structures that are similar to native valve structures, said adaptive regeneration system comprising a material component and physical structure component, said adaptive regeneration system material component comprising an extracellular matrix (ECM) composition, said ECM composition comprising acellular ECM from a mammalian tissue source, said adaptive regeneration system physical structure component comprising a valve member comprising a proximal valve annulus engagement end and a distal end, said proximal valve annulus engagement end of said valve member being configured to engage said AV valve annulus region, said proximal valve annulus engagement end comprising a circumferential ribbon connection region and a plurality of ribbons projecting from said circumferential ribbon connection region toward said distal end of said valve member, each of said plurality of ribbons comprising proximal and distal ends, a first edge region extending from said proximal end of each of said plurality of ribbons to said distal end of each of said plurality of ribbons and a second edge region extending from said proximal end of each of said plurality of ribbons to said distal end of each of said plurality of ribbons, said proximal end of each of said plurality of ribbons being connected to said circumferential ribbon connection region, whereby said first and second edge regions of said plurality of elongated ribbon members form a plurality of flow modulating regions, said distal ends of said plurality of elongated ribbon members being adapted to engage a cardiovascular structure, wherein said distal ends of said plurality of elongated ribbon members are positioned proximate each other in a constrained relationship and said fluid flow through said distal ends of said plurality of elongated ribbon members is restricted while said fluid flow is allowed to be transmitted through said fluid flow modulating regions when said fluid flow modulating regions are in an open position, said valve member being configured to transition from an expanded position when said proximal valve annulus engagement end of said valve member is engaged to said AV valve annulus region and receives said fluid flow therein, and said fluid flow exhibits a first positive flow pressure of said plurality of positive flow pressures, to a collapsed position when said fluid flow exhibits a first negative flow pressure of said plurality of negative flow pressures, said plurality of fluid flow modulating regions being configured to transition from said open position when said valve member is in said expanded position, wherein said plurality of fluid flow modulating regions allow said fluid flow to be transmitted through said valve member, to a closed position when said valve member is in said collapsed position, wherein said plurality of fluid flow modulating regions restrict said fluid flow through said valve member.

2. The prosthetic valve of claim 1, wherein said mammalian tissue source is selected from the group consisting of small intestine submucosa (SIS), urinary bladder submucosa (UBS), urinary basement membrane (UBM), liver basement membrane (LBM), stomach submucosa (SS), mesothelial tissue, placental tissue and cardiac tissue.

3. The prosthetic valve of claim 1, wherein said ECM composition further comprises at least one exogenously added biologically active agent.

4. The prosthetic valve of claim 3, wherein said biologically active agent comprises a cell selected from the group consisting of a human embryonic stem cell, fetal cardiomyocyte, myofibroblast, and mesenchymal stem cell.

5. The prosthetic valve of claim 3, wherein said biologically active agent comprises a growth factor selected from the group consisting of a transforming growth factor-alpha (TGF-α), transforming growth factor-beta (TGF-β), fibroblast growth factor-2 (FGF-2), and vascular endothelial growth factor (VEGF).

6. The prosthetic valve of claim 1, wherein said ECM composition further comprises a pharmacological agent.

7. The prosthetic valve of claim 6, wherein said pharmacological agent comprises an agent selected from the group consisting of an antibiotic, anti-viral, analgesic, anti-inflammatory, anti-neoplastic, anti-spasmodic, anti-coagulant and anti-thrombotic agent.

8. A prosthetic valve for modulating fluid flow through an atrioventricular (AV) valve annulus region during cardiac cycles of a heart, said fluid flow exhibiting a plurality of positive and negative flow pressures during said cardiac cycles, said prosthetic valve comprising:

a remodelable biological tissue structure, said remodelable biological tissue structure defining a continuous tubular shaped sheet member, said tubular shaped sheet member comprising an extracellular matrix (ECM) composition, said ECM composition comprising acellular ECM from a mammalian tissue source, said tubular shaped sheet member further comprising a proximal valve annulus engagement end and a distal end, said proximal valve annulus engagement end being configured to engage said AV valve annulus region, said proximal valve annulus engagement end comprising a circumferential ribbon connection region and a plurality of ribbons projecting from said circumferential ribbon connection region toward said sheet member distal end, each of said plurality of ribbons comprising proximal and distal ends, a first edge region extending from said proximal end of each of said plurality of ribbons to said distal end of each of said plurality of ribbons and a second edge region extending from said proximal end of each of said plurality of ribbons to said distal end of each of said plurality of ribbons, said proximal end of each of said plurality of ribbons being connected to said circumferential ribbon connection region, whereby said first and second edge regions of said plurality of elongated ribbon members form a plurality of flow modulating regions, said distal ends of said plurality of elongated ribbon members being adapted to engage a cardiovascular structure, wherein said distal ends of said plurality of elongated ribbon members are positioned proximate each other in a constrained relationship and said fluid flow through said distal ends of said plurality of elongated ribbon members is restricted while said fluid flow is allowed to be transmitted through said fluid flow modulating regions when said fluid flow modulating regions are in an open position, said tubular shaped sheet member being configured to transition from an expanded position when said proximal valve annulus engagement end of said tubular shaped sheet member is engaged to said AV valve annulus region and receives said fluid flow therein, and said fluid flow exhibits a first positive flow pressure of said plurality of positive flow pressures, to a collapsed position when said fluid flow exhibits a first negative flow pressure of said plurality of negative flow pressures, said plurality of fluid flow modulating regions being configured to transition from said open position when said tubular shaped sheet member is in said expanded position, wherein said plurality of fluid flow modulating regions allow said fluid flow to be transmitted through said tubular shaped sheet member, to a closed position when said tubular shaped sheet member is in said collapsed position, wherein said plurality of fluid flow modulating regions restrict said fluid flow through said tubular shaped sheet member.

9. The prosthetic valve of claim 8, wherein said mammalian tissue source is selected from the group consisting of small intestine submucosa (SIS), urinary bladder submucosa (UBS), urinary basement membrane (UBM), liver basement membrane (LBM), stomach submucosa (SS), mesothelial tissue, placental tissue and cardiac tissue.

* * * * *